US006859335B1

(12) United States Patent
Lai et al.

(10) Patent No.: US 6,859,335 B1
(45) Date of Patent: Feb. 22, 2005

(54) METHOD OF PROGRAMMED DISPLACEMENT FOR PROLONG USAGE OF OPTICAL ELEMENTS UNDER THE IRRADIATION OF INTENSIVE LASER BEAMS

(76) Inventors: Ming Lai, P.O. Box 10845, Pleasanton, CA (US) 94588; Zhimin Qu, 5595 Springhouse Dr. Apt. 25, Pleasanton, CA (US) 94588; Mehrdad Mohebi, 5216 Spoleto Ct., Pleasanton, CA (US) 94588

( * ) Notice: Subject to any disclaimer, the term of this patent is extended or adjusted under 35 U.S.C. 154(b) by 1 day.

(21) Appl. No.: 10/714,274

(22) Filed: Nov. 13, 2003

Related U.S. Application Data
(60) Provisional application No. 60/428,213, filed on Nov. 20, 2002.

(51) Int. Cl.[7] .......................... G02B 27/02; G01B 9/00; G01B 11/02
(52) U.S. Cl. ...................... 359/800; 359/798; 356/515; 356/124
(58) Field of Search ................................ 359/800, 798; 356/124, 125, 126, 127, 515, 520, 512

(56) References Cited

U.S. PATENT DOCUMENTS

| | | | |
|---|---|---|---|
| 5,144,630 A | 9/1992 | Lin | 372/22 |
| 5,401,948 A | 3/1995 | Krichever et al. | 235/462.35 |
| 5,825,562 A | 10/1998 | Lai et al. | 359/822 |
| 6,031,854 A | 2/2000 | Lai | 372/22 |
| 6,373,578 B1 * | 4/2002 | Nishikawa | 356/515 |
| 6,577,387 B2 * | 6/2003 | Ross et al. | 356/124 |

FOREIGN PATENT DOCUMENTS

| | | |
|---|---|---|
| WO | WO 99/55216 | 11/1999 |
| WO | WO 00/04952 | 2/2000 |

* cited by examiner

*Primary Examiner*—Timothy J Thompson

(57) ABSTRACT

The present invention contemplates a programmed displacement to prolong the usage life of UV crystal for deep UV generation by displacing step by step the crystal with interval between steps much shorter than the degradation time of the crystal. Meanwhile, the present invention contemplates the programmed displacement to obtain stable UV generation by avoiding defect locations of the crystal. Further, the present invention contemplates the programmed displacement to achieve optimal stability in UV power for each layer of UV ablation in photo-refractive surgery.

20 Claims, 2 Drawing Sheets

METHOD OF PROGRAMMED DISPLACEMENT FOR PROLONG USAGE OF OPTICAL ELEMENTS UNDER THE IRRADIATION OF INTENSIVE LASER BEAMS

This application claims the benefit of U.S. Provisional Application No. 60/428,213, filed on Nov. 20, 2002.

TECHNICAL FIELD

The present invention relates to a device and method for prolonging the usage life of an optical element under the irradiation of an intensive laser beam by programmed displacement of the optical element. In particularly, the present invention relates to a delay or complete elimination of laser beam damage on nonlinear optical crystals, such as BBO, LBO, CLBO, KTP, KD*P, and KDP.

BACKGROUND

When a nonlinear optical crystal or any optical element is irradiated with an intensive laser beam, the performance of the crystal or optical element may degrade with time. The higher the incident laser beam intensity, the faster it degrades. This degradation process is usually referred to as laser induced damage. Laser induced damage may happen on the surface of or inside an optical element.

There are many mechanisms leading to laser induced damage in optical element. Some mechanisms lead to instance damages, while some other mechanisms lead to degradation over time in the early stage before a complete damage. For high intensity UV generation in BBO, for example, color center or other defects may be induced and accumulated in an early stage before a sudden damage happen.

In U.S. Pat. No. 5,825,562 to Lai et al, a continuous motion is used to prolong usage of optical elements under the irradiation of intensive laser beam. In an embodiment of UV generation in BBO crystal, Lai et al describe to scan continuously the crystal in a circular area and the usage life of the crystal has been increased significantly. The continuous motion enables a much larger interaction area of the laser beam on the crystal surface and increases the time interval for laser induced thermal or mechanical impacts to relax at any specific spot on the crystal surface. The continuous motion may also allow the laser induced color center and other defects to relax before these defects accumulate and become permanent.

One problem stemming from a continuous motion is a possible fluctuation in the generated UV beam, due to imperfection on the surface of or inside the crystal. Experiment has found it not realistic to expect a crystal having no initial defect and no dust particle over a relatively large area. Also, micro-crack or other micro-defect may grow under irradiation of intensive laser beam or generated UV laser beam. Besides, experiment shows that motion-induced fluctuation in deep UV generation is small but can be troublesome to delicate applications like photo-refractive surgery. This motion-induced fluctuation may stem from residual variation in mechanical alignment and non-uniformity of material or coating of the optical element.

On the other hand, a prior art practice displaces the UV crystal step by step while at each step the crystal stays for a predetermined exposure time or until a predetermined degradation. The crystal displaces to each step location only once and the step location can not be reused after the location has been exposed. This practice works well if the crystal degradation time is relatively long, say several hours or days. This practice becomes not practical if the crystal degradation time is short, say several minutes or tens of minutes.

SUMMARY

The present invention contemplates a programmed displacement of the UV crystal to solve the above-identified problems. The present invention contemplates to make the crystal displacement in a programmable fashion controlled by a microprocessor. The crystal is first scanned to map all defect locations and these defect locations are recorded in the microprocessor memory. The crystal is then displaced step by step over the non-defect area. At each step location, the crystal stays stationary for a predetermined period of time to eliminate motion-induced power fluctuation of UV generation. The predetermined period of time is much shorter than the degradation time of the crystal at the given irradiation of the intensive laser beam. The crystal is displaced step by step over the non-defect area again and again in a programmable fashion. Meanwhile, any new defect location detected is added into the microprocessor memory and will be avoided in the future scans. This way, temporarily stable UV generation can be obtained while the usage life of the UV crystal can be prolonged due to the consecutive displacement with programmed short interval between displacement steps. This approach is extremely useful for deep UV generation of a solid state laser beam for photo-refractive surgery, where UV fluctuation shall be minimized and minimal UV fluctuation is desirable within each layer of UV ablation.

In accordance with the present invention, a method of programmed displacement for prolong usage of an optical element under the irradiation of an intensive laser beam comprises the steps of:

directing said intensive laser beam in a predetermined direction toward and passing through said optical element;

providing a driving mechanism to displace said optical element with respect to said intensive laser beam;

providing a microprocessor control unit to control said driving mechanism to move in a step by step fashion;

providing a monitoring means to monitor the intensity of an output beam from said optical element;

scanning said optical element to determine initial defect locations of said optical element;

storing initial defect locations in said microprocessor control unit;

displacing said optical element step by step over the non-defect area of said optical element with a predetermined short interval between steps; and repeating said step of displacing said optical element again and again over said non-defect area of said optical element.

Accordingly, an objective of the present invention is to provide a new and improved method to prolong the usage of optical elements under the irradiation of intensive laser beams and meanwhile to obtain temporally stable output from the optical elements.

Another objective of the present invention is to provide a new and improved method to employ a programmed displacement to prolong the usage lifetime of optical elements under the irradiation of intensive laser beams.

A further objective of the present invention is to provide a new and improved method to obtain temporarily stable deep UV laser beam from an UV generation in a BBO or CLBO crystal.

Another further objective of the present invention is to provide a new and improved method to obtain temporarily stable deep UV laser beam for photo-refractive surgery.

The above and other objectives and advantages of the invention will become more apparent in the following drawings, detailed description, and claims.

DETAILED DESCRIPTION

Figure 1:
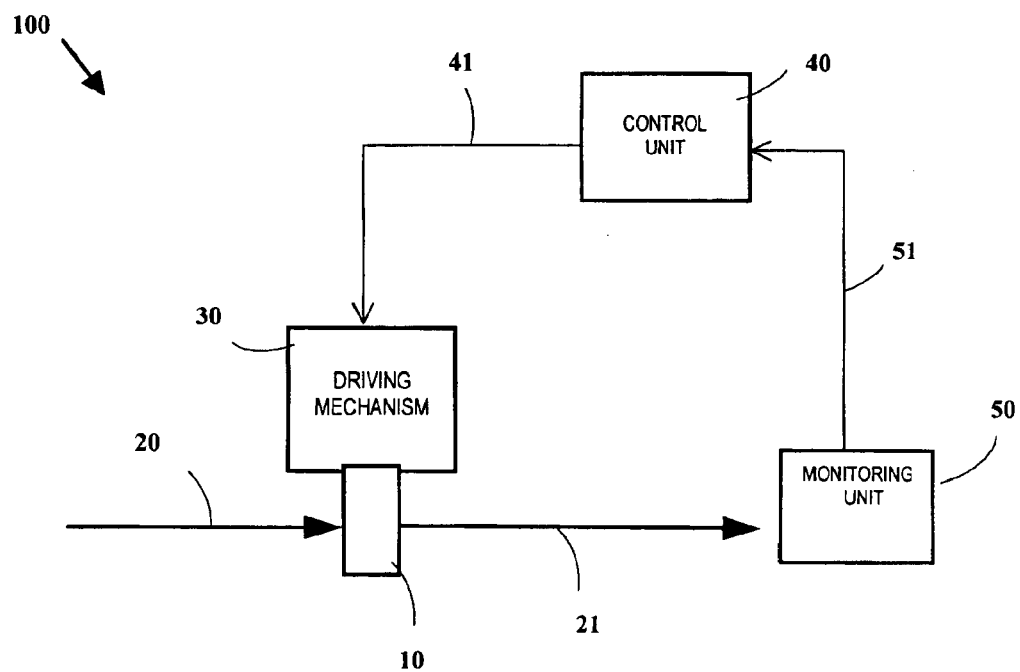
FIG. 1 is a block diagram showing a design of programmed displacement for prolonging usage of an optical element under the irradiation of an intensive laser beam, in accordance with the present invention.

FIG. 1 is a block diagram 100 showing a design concept of programmed displacement for prolonging usage of an optical element 10 under the irradiation of an intensive laser beam 20, in accordance with the present invention. The block diagram 100 includes an optical element 10, an intensive laser beam 20, a transmitted or output laser beam 21, a driving mechanism 30, a control unit 40, and a monitoring unit 50.

The optical element 10 can be a piece of UV optics, a laser crystal, or a nonlinear optical crystal. Examples of laser crystal include Nd:YLF, Cr:LiSAF, Cr:YAG, and Ho:YAG. Examples of nonlinear optical crystals include BBO, LBO, CLBO, KTP, KD*P, and KDP crystals.

The intensive laser beam 20 can be a CW or pulsed laser beam with predetermined spot size, wavelength, and power density. The wavelength of the intensive laser beam 20 can be in the range from 100 nm to 1 micron. For a pulsed laser beam, the intensive laser beam 20 can have pulse duration in the range of 1 fs to 10 ms.

The transmitted or output laser beam 21 from the optical element 10 may have the same or different wavelength component from the incident intensive laser beam 20. Due to a number of mechanisms known to those skilled in the art, the optical element 10 degrade over time under the irradiation of the intensive laser beam 20 if the optical element 10 stays stationary.

The driving mechanism 30 is operationally connected to the optical element 10 and can displace laterally the optical element 10 under the commanded signal 41 from the control unit 40. The driving mechanism 30 may simply consist of a x-y translation stage driven by two step-motors.

The monitoring unit 50 detects a component of the transmitted or output beam 21 from the optical element 10. The power level of the detected component or its stability can be crucial in many applications, such as the UV beam produced in a BBO crystal through harmonic generation. The output signal 51 from the monitoring unit 50 indicates the performance status of the optical element 10.

The control unit 40 includes a microprocessor or other computer means. It reads in and processes the signal 51 from the monitoring unit 50 and then generates through computer program a control signal 41 to drive the driving mechanism 30.

In the present invention, the control unit 40 drives first the driving mechanism 30 to scan laterally the optical element 10 step by step over a certain area of interest. The setup is such that the transmitted or output beam 21 shall remain unchanged if the optical element 10 is perfect. Any defect in the optical element 10 thus causes a fluctuation in the detected signal 51. The control unit 40 records each fluctuation in the detected signal 51 and correlates it with an instant position of the optical element 10. By this way, the control unit 40 can map the location of every initial defect within the area of interest. The control unit 40 saves these locations of the defects in its memory for later reference.

A computer program of the control unit 40 can then produce a programmed displacement of the optical element 10 to displace step by step over the non-defect area of the optical element 10. The programmed displacement can take a serial of linear paths or a serial of irregular loops. At each step of displacement, the optical element 10 stays for a short period of time to obtain optimal stability. The interval between the steps is correlated with an application requirement of the output beam 21. This interval shall be much shorter than the degradation time of the optical element 10 under the irradiation of the intensive laser beam 20 and shall be in the range from milliseconds to minutes.

The computer program of the control unit 40 can further produce a programmed scan of the optical element 10 to scan again and again over the non-defect area of the optical element 10. Meanwhile, the control unit 40 continuously reads in signal 51 from the monitoring unit 50 to identify new defects that may develop during the operation. The location of each new defect is added into the memory of the control unit 40. The control unit 40 can thus avoid these locations of new defects in the future displacement and scan.

Figure 2:
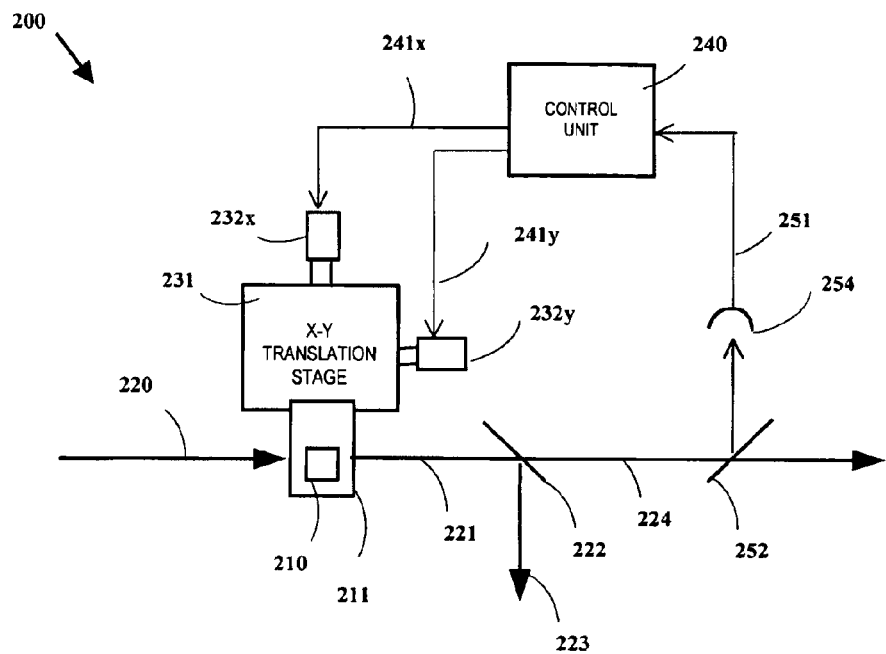
FIG. 2 shows a schematic diagram of a setup for programmed displacement of a BBO crystal in deep UV generation, in accordance with one embodiment of the present invention.

FIG. 2 is a schematic diagram showing a setup 200 for programmed displacement of a BBO crystal 210 in deep UV generation, in accordance with one embodiment of the present invention. A direct application of deep UV generation is to produce a deep UV laser beam from a solid state laser for photo-refractive surgery, as described in U.S. Pat. No. 6,031,854 to Lai.

The BBO crystal 210 is mounted in a crystal holder 211. An intensive laser beam 220 impinges into the BBO crystal 210 to produce a deep UV laser beam through harmonic generation. As for photo-refractive surgery, the intensive laser beam 220 can have a fundamental wavelength around 420 nm and the generated deep UV laser beam 224 has a wavelength around 210 nm. The pulse duration, pulse repetition rate, and pulse energy of the intensive laser beam 220 can be, respectively, about 0.1 ns to 100 ns, about 0.1 kHz to 100 kHz, and about 0.1 mJ to 20 mJ. The preparation and alignment of BBO for deep UV generation are known to those skilled in the art.

A dichromatic beam splitter 222 separates beam 224 of UV wavelength from beam 223 of fundamental wavelength. A sampling beam splitter 252 directs a small portion of beam 224 onto an UV detector 254. The output signal 251 from the UV detector 254 carries the information of fluctuation of the deep UV laser beam 224.

A control unit 240 reads in the signal 251 from the UV detector 254 to monitor the performance of the deep UV generation from the BBO 210. The control unit 240 first produces driving signal $241x$ and $241y$ to drive respectively step-motor $232x$ and $232y$. Step-motor $232x$ and $232y$ in turns drive a x-y translation stage 231, onto which the crystal holder 211 is affixed. For any given position of the step-motors $231x$ and $231y$, the control unit 240 reads in the signal 251 to determine the UV output at that position. This way, the control unit 240 can identify the corresponding position of any defect of the BBO crystal 210. The control unit 240 saves these locations of the defects in its memory for later reference.

A computer program of the control unit 240 can then produce a programmed displacement of the BBO crystal 210 to displace step by step over the non-defect area. At each step of displacement, the BBO crystal 210 stays for a short period of time to obtain optimal stability. For UV ablation in photo-refractive surgery, this short period of time can be correlated to the scanning time of one layer of ablation. For a solid state operated at 1 kHz, this short period of time is about 10 ms to 1 s.

The computer program of the control unit 240 can further produce a programmed displacement of the BBO crystal 210 to scan again and again over its non-defect area. Meanwhile, the control unit 240 continuously reads in signal 251 from the UV photo detector 254 to identify new defects that may develop during the operation. The location of each new defect is added into the memory of the control unit 240. The control unit 240 can thus avoid these locations of new defects in the further displacement and scan.

Therefore, what can be achieved with this programmed displacement for photo-refractive surgery is:
1. to prolong the usage life of the BBO crystal by displacing step by step the crystal with interval between steps much shorter than the degradation time of the crystal;
2. to obtain stable UV generation by avoiding defect locations of the crystal; and
3. to achieve optimal stability in UV power for each layer of UV ablation by correlating the step displacement of the crystal with each layer scanning of UV ablation.

Although the present invention has been described with specific reference to embodiments, by way of illustration and for clarity of understanding, various modifications can be made without departing from the scopes of the appended claims.

What is claimed is:

1. A method of programmed displacement for prolong usage of an optical element under the irradiation of an intensive laser beam, comprising the steps of:
    directing said intensive laser beam in a predetermined direction toward and passing through said optical element;
    providing a driving mechanism to displace said optical element with respect to said intensive laser beam;
    providing a microprocessor control unit to control said driving mechanism to move in a step by step fashion;
    providing a monitoring means to monitor the intensity of an output beam from said optical element;
    scanning said optical element to determine initial defect locations of said optical element;
    storing initial defect locations in said microprocessor control unit;
    displacing said optical element step by step over the non-defect area of said optical element with a predetermined short interval between steps; and
    repeating said step of displacing said optical element again and again over said non-defect area of said optical element.

2. A method as in claim 1 wherein said optical element is a nonlinear optical crystal selected from BBO, LBO, CLBO, KTP, KD*P, and KDP crystals.

3. A method as in claim 1 wherein said optical element is an UV optics.

4. A method as in claim 1 wherein said optical element is a laser crystal selected from Nd:YLF, Cr:LiSAF, Cr:YAG, and Ho:YAG.

5. A method as in claim 1 wherein said intensive laser beam is delivered from a CW laser.

6. A method as in claim 1 wherein said intensive laser beam is delivered from a pulsed laser.

7. A method as in claim 1 wherein said intensive laser beam has a pulse duration in the range of 1 fs to 10 ms.

8. A method as in claim 1 wherein said intensive laser beam has a wavelength ranging from 100 nm to 1 micron.

9. A method as in claim 1 wherein said intensive laser beam has a wavelength around 420 nm and said output beam has a wavelength around 210 nm.

10. A method as in claim 1 wherein said intensive laser beam has a pulse duration ranging from 0.1 ns to 100 ns.

11. A method as in claim 1 wherein said intensive laser beam has a pulse repetition rate ranging from 0.1 kHz to 100 kHz.

12. A method as in claim 1 wherein said intensive laser beam has a pulse energy ranging from 0.1 mJ to 20 mJ.

13. A method as in claim 1 wherein said driving mechanism consists of two step-motors.

14. A method as in claim 1 wherein said monitoring means is an UV photo detector.

15. A method as in claim 1 wherein said step of displacing said optical element includes displacing said optical element in a serial of linear paths.

16. A method as in claim 1 wherein said step of displacing said optical element includes displacing said optical element in a serial of irregular loops.

17. A method as in claim 1 wherein said predetermined short interval is in the range of 1 ms to 1 minute.

18. A method as in claim 1 wherein said predetermined short interval is correlated with the scan time needed for one layer of UV ablation in a refractive surgery.

19. A method as in claim 1, further comprising the steps of:
    monitoring said intensity of said output beam from said optical element to determine newly developed defects of said optical element;
    adding locations of said newly developed defects to said microprocessor control unit.

20. An apparatus of programmed displacement for prolong usage of an optical element under the irradiation of an intensive laser beam, comprising:
    said intensive laser beam directed in a predetermined direction toward and passing through said optical element;
    a driving mechanism to displace said optical element with respect to said intensive laser beam;
    a microprocessor control unit to control said driving mechanism to move in a step by step fashion;
    monitoring means to monitor the intensity of an output beam from said optical element;
    wherein said optical element is first scanned to determine initial defect locations of said optical element, said microprocessor control unit then stores said initial defect locations and displaces said optical element step by step over the non-defect area of said optical element with a predetermined short interval between steps, and said microprocessor control unit further repeats said displacement of said optical element again and again over said non-defect area of said optical element.

* * * * *